United States Patent [19]

Gates et al.

[11] 4,345,932

[45] Aug. 24, 1982

[54] HERBICIDES

[75] Inventors: Peter S. Gates, Cambridge; John Gillon, Great Shelford; David T. Saggers, Saffron Walden, all of England

[73] Assignee: Fisons Limited, London, England

[21] Appl. No.: 804,752

[22] Filed: Jun. 8, 1977

Related U.S. Application Data

[60] Continuation of Ser. No. 648,161, Jan. 12, 1976, Pat. No. 4,072,495, which is a continuation-in-part of Ser. No. 275,256, Jul. 26, 1972, abandoned, which is a division of Ser. No. 826,274, May 20, 1969, Pat. No. 3,689,507.

[30] Foreign Application Priority Data

| May 24, 1968 [GB] | United Kingdom | 24858/68 |
| Feb. 8, 1969 [GB] | United Kingdom | 6951/69 |
| Apr. 8, 1969 [GB] | United Kingdom | 7985/69 |

[51] Int. Cl.³ .................................................. A01N 43/08
[52] U.S. Cl. .................................................. 71/88; 71/92; 71/111
[58] Field of Search .............................. 71/88, 92, 111

[56] References Cited

U.S. PATENT DOCUMENTS

| 3,940,259 | 2/1976 | Richter et al. | 71/88 |
| 3,941,581 | 3/1976 | Teach | 71/118 |
| 3,942,972 | 3/1976 | Richter et al. | 71/88 |
| 3,961,936 | 6/1976 | Westphal et al. | 71/93 |

*Primary Examiner*—Catherine L. Mills
*Attorney, Agent, or Firm*—Wenderoth, Lind & Ponack

[57] ABSTRACT

5-Benzofuranyl esters of the general formula

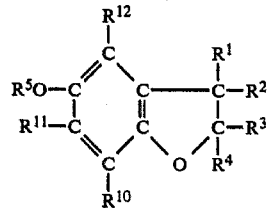

wherein the substituents are as defined in the specification, possess physiological activity, particularly plant physiological activity and may be used as herbicides, plant growth regulants, fungicides, insecticides and anthelmintics.

44 Claims, No Drawings

HERBICIDES

This application is a continuation of application Ser. No. 648,161, filed Jan. 12, 1976, now U.S. Pat. No. 4,072,495 which application is a continuation-in-part of application Ser. No. 275,256, filed July 26, 1972 (now abandoned), which application is in turn a divisional of application Ser. No. 826,274, filed May 20, 1969 (now U.S. Pat. No. 3,689,507).

The present invention relates to certain new 5-benzofuranyl esters which have been found to possess physiological activity, particularly plant physiological activity, to their preparation and to agricultural and other compositions containing the same. These compounds may be used as herbicides and as plant growth regulants. The compounds may also be used as fungicides, insecticides and anthelmintics.

Accordingly the present invention is for the 5-benzofuranyl esters of the general formula:

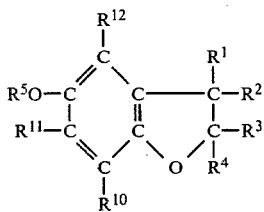

wherein $R^1$, $R^2$ and $R^3$ are the same or different and may be hydrogen or alkyl (for example of 1–6 carbon atoms such as methyl or ethyl), or $R^1$ and $R^2$ together or $R^2$ and $R^3$ together may form an alkylene chain (for example of 2–5 carbon atoms); $R^4$ is hydroxy, alkoxy (for example of 1–8 carbon atoms such as methoxy or butoxy), substituted alkoxy (for example of 1–8 carbon atoms substituted by halogen or alkoxy such as chloroethoxy or methoxyethoxy), alkenyloxy (for example of 2–4 carbon atoms such as allyloxy), alkylthio (for example of 1–4 carbon atoms such as methylthio or ethylthio), substituted alkenyloxy (for example of 2–4 carbon atoms substituted by halogen such as chloroallyloxy), alkynyloxy (for example of 2–6 carbon atoms such as propargyloxy or butynyloxy), substituted alkynyloxy (for example of 2–4 carbon atoms substituted by halogen such as chlorobutynyloxy), aryloxy (for example phenoxy), substituted aryloxy (for example substituted by nitro or halogen such as nitrophenoxy), the group $NR^6R^7$ in which $R^6$ and $R^7$ are alkyl (for example of 1–4 carbon atoms such as methyl or ethyl) or substituted alkyl (for example of 1–4 carbon atoms substituted by halogen such as haloethyl) or together with the nitrogen atom form a heterocyclic ring, substituted or unsubstituted such as morpholine, pyrrolidine, piperidine or methyl piperazine, the group $—OCOR^{13}$, the group $—OSO_2R^{14}$ or the group $—O—O—R^{15}$, in which $R^{13}$ is alkyl (for example of 1–4 carbon atoms such as methyl or isopropyl), alkenyl (for example of 2–4 carbon atoms such as allyl), alkynyl (for example of 2–4 carbon atoms such as propargyl), substituted alkyl, alkenyl or alkynyl (for example aryloxy or halogen substituted such as trifluoromethyl, phenoxymethyl or chloroethyl), aryl (for example phenyl), substituted aryl (for example halogen or alkyl substituted such as chlorophenyl or tolyl), alkylamino (for example of 1–4 carbon atoms such as methylamino), dialkylamino (for example of 2–8 carbon atoms such as dimethylamino), alkoxy (for example of 1–6 carbon atoms such as methoxy or ethoxy), aryloxy (for example phenoxy), arylamino (for example phenylamino), substituted arylamino (for example substituted by halogen such as chlorophenylamino), substituted alkoxy (for example of 1–6 carbon atoms substituted by halogen or alkoxy such as methoxyethoxy), substituted aryloxy (for example halogen substituted such as chlorophenoxy), alkenyloxy (for example of 2–4 carbon atoms such as allyloxy), substituted alkenyloxy (for example of 2–4 carbon atoms substituted by halogen such as chloroallyloxy), alkynyloxy (for example of 2–4 carbon atoms such as propargyloxy) or substituted alkynyloxy (for example of 2–4 carbon atoms substituted by halogen such as chlorobutynyloxy), in which $R^{14}$ is alkyl (for example of 1–4 carbon atoms such as methyl or ethyl), substituted alkyl (for example of 1–4 carbon atoms substituted by halogen such as chloroethyl), aryl (for example phenyl), substituted aryl (for example halogen, nitro or alkyl substituted such as chlorophenyl, nitrophenyl of tolyl), in which $R^{15}$ is alkyl (for example of 1–4 carbon atoms such as methyl, isopropyl or tertiary butyl), alkenyl (for example of 2–4 carbon atoms such as allyl) or alkynyl (for example of 2–4 carbon atoms such as propargyl); or $R^3$ and $R^4$ together represent an oxygen atom or the group $=NR^{16}$ in which $R^{16}$ is alkyl (for example of 1–4 carbon atoms such as methyl or isopropyl) or cycloalkyl (for example of 5 or 6 carbon atoms such as cyclohexyl); $R^5$ is the group $R^8CO—$ or the group $R^9SO_2—$ or the group $R^9SO—$ in which $R^8$ is halogen substituted alkyl (for example of 1–4 carbon atoms such as chloromethyl, dichloroethyl, trichloroethyl or bromoethyl) and $R^9$ is alkyl (for example of 1–4 carbon atoms such as methyl or ethyl), substituted alkyl (for example of 1–4 carbon atoms substituted by halogen or alkoxy such as chloromethyl, methoxypropyl and bromoethyl) aryl (for example phenyl) or substituted aryl (for example substituted halogen or alkyl such as chlorophenyl or tolyl); and $R^{10}$, $R^{11}$ and $R^{12}$ are the same or different and are hydrogen, alkyl (for example of 1–4 carbon atoms such as methyl, ethyl or isopropyl), halogen (for example chlorine or bromine), cyano, acyl (for example of 2–6 carbon atoms such as acetyl) or alkoxy (for example of 1–4 carbon atoms such as methoxy).

The present invention is also for a physiological active composition and particularly a herbicidal composition or plant growth composition which contains as an active component a benzofuranyl ester as identified above. The physiologically active composition suitably also contains at least one material selected from the group comprising carriers, wetting agents, inert diluents and solvents.

The present invention is also for the treatment of plants, the soil, land or aquatic areas, or materials which comprises applying thereon or thereto a benzofuranyl ester or a plant physiologically active composition as identified above.

The substituted benzofuranyl esters according to the present invention generally possess physiological activity. These compounds are useful as herbicides, and also as plant growth regulants. They are also fungicides, insecticides and anthelmintics.

The benzofuranyl esters identified above have been found to be of particular value as selective herbicides for pre-emergence use and also are useful for post-emergence use. With some crops, pre-emergence use is of greater importance. At higher concentrations the compounds may also be used as total weedkillers. At much lower concentrations the compounds may be used as plant growth regulators.

According to a preferred embodiment the present invention is for the benzofuranyl esters of the general formula:

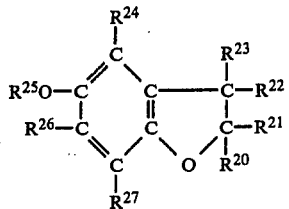

wherein $R^{20}$ is selected from dialkylamino of 2-4 carbon atoms, piperidino, morpholino, 4-methylpiperazinc, pyrrolidino, hydroxy, alkoxy of 1-4 carbon atoms, alkenyloxy of 2-4 carbon atoms, alkynyloxy of 2-4 carbon atoms, alkoxyalkoxy, of 2-8 carbon atoms, alkylthio of 1-4 carbon atoms, $—OCOR^{28}$, $—SO_2R^{29}$ and $—O—O—R^{29}$, where $R^{28}$ is alkyl of 1-4 carbon atoms or phenyl; where $R^{29}$ is alkyl of 1-4 carbon atoms; where $R^{21}$ is hydrogen or together with $R^{20}$ represents an oxygen atom, where $R^{22}$ and $R^{23}$ represent hydrogen or alkyl of 1-4 carbon atoms; where $R^{25}$ represents $R^{30}SO_2—$ where $R^{30}$ is alkyl of 1-4 carbon atoms; and where $R^{24}$, $R^{26}$ and $R^{27}$ represent hydrogen, halogen (for example chloro or bromo) or alkyl of 1-4 carbon atoms.

According to one embodiment, the present invention is for the benzofuranyl esters according to the general formula above in which $R^1$, $R^2$ and $R^3$ are selected from hydrogen and alkyl, or $R^1$ and $R^2$ together or $R^2$ and $R^3$ together form an alkylene chain; where $R^4$ is hydroxy, alkoxy, substituted alkoxy, alkenyloxy, alkylthio or $—NR^6R^7$, and wherein $R^5$, $R^6$, $R^7$, $R^8$, $R^9$, $R^{10}$, $R^{11}$ and $R^{12}$ have the significance indicated above.

According to another embodiment, the present invention is for the benzofuranyl esters according to the general formula above in which $R^1$, $R^2$ and $R^3$ are selected from hydrogen and alkyl, or $R^1$ and $R^2$ together or $R^2$ and $R^3$ together form an alkyene chain; where $R^4$ is $—OCOR^{13}$ or $—OSO_2R^{14}$, and wherein $R^5$, $R^{10}$, $R^{11}$, $R^{12}$, $R^{13}$ and $R^{14}$ have the significance indicated above.

According to another embodiment, the present invention is for the benzofuranyl esters according to the general formula above in which $R^1$, $R^2$ and $R^3$ are selected from hydrogen and alkyl, or $R^1$ and $R^2$ together or $R^2$ and $R^3$ together form an alkylene chain; where $R^4$ is the group $—O—O—R^{15}$, or $R^3$ and $R^4$ together represent an oxygen atom or the group $=NR^{16}$; wherein $R^5$, $R^8$, $R^9$, $R^{10}$, $R^{11}$, $R^{12}$, $R^{15}$ and $R^{16}$ have the significance indicated above.

The 5-benzofuranyl esters according to the present invention may be prepared by the reaction between the corresponding 5-hydroxybenzofuran of the formula:

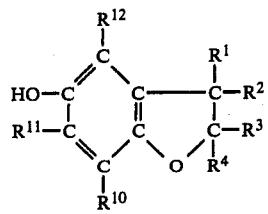

and an acylating agent of the formula $R^5X$ or $(R^5)_2O$ where X is halogen, particularly chlorine. The reaction is preferably carried out in the presence of an acid acceptor such as an organic base (for example pyridine or triethylamine) or an alkali (for example an alkali metal carbonate or bicarbonate).

The benzofuranyl esters where $R^4$ is the group $—OCOR^{13}$ or $—OSO_2R^{14}$ may be prepared by reacting the corresponding compound where $R^4$ is hydroxy, with a compound of the formula $R^{13}COX$ or $R^{14}SO_2X$ (in which X is halogen), the groups $R^1$-$R^{14}$ having the significance indicated above. In the case where $R^{13}$ is a hydrocarbon group, the compound $R^{13}COX$ is an acyl halide and the product is a 2-acyloxybenzofuran; in the case where $R^{13}$ is a substituted amino group, the compound $R^{13}COX$ is a substituted carbamoylhalide and the product is a 2-carbamoyloxybenzofuran; in the case where $R^{13}$ is an alkoxy group or aryloxy group, the compound $R^{13}COX$ is a haloformate and the product is a carbonate ester.

Where $R^{13}$ is an alkylamino group, the compounds can also be prepared by the reaction between a 2-hydroxybenzofuran of the formula above and an alkyl isocyanate.

Where $R^{13}$ is a hydrocarbon group, the compounds can also be prepared by the reaction of a 2-hydroxybenzofuran of the above formula or a corresponding 2-alkoxybenzofuran with an acid anhydride of the formula $(R^{13}CO)_2O$.

The benzofuranyl esters where $R^4$ is the group $—O—O—R^{15}$ may be prepared by reacting the corresponding compound where $R^4$ is hydroxy, with a hydroperoxide of the formula $R^{15}OOH$.

The benzofuranyl esters where $R^3$ and $R^4$ together represent the group $=NR^{16}$ may be prepared by reacting a ketenimine with a benzoquinone to form the 2-imino-5-hydroxybenzofuran according to the equation:

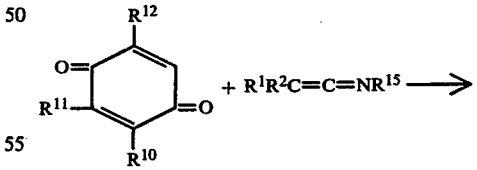

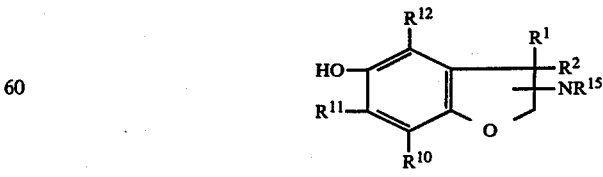

which is then reacted with a compound of the formula $R^5Cl$ to give the desired compound.

The benzofuranyl esters where $R^3$ and $R^4$ together represent an oxygen atom may be prepared by the oxidation of the corresponding compound where $R^3$ is hydrogen and $R^4$ is hydroxy, alkoxy, —$NR^6R^7$ or —O-$COR^{13}$ (where $R^6$ and $R^7$ are alkyl, substituted alkyl or heterocyclic and $R^{13}$ is alkyl, alkenyl or alkynyl, substituted or unsubstituted), for example using chromic oxide in acid, or by the hydrolysis of the corresponding compound in which $R^3$ and $R^4$ together represent =$NR^{16}$.

The benzofuranyl compounds are generally water insoluble and may be formulated in any of the conventional ways for insoluble compounds.

If desired the benzofuranyl esters may be dissolved in a water immiscible solvent, such as for example a high boiling hydrocarbon, suitably containing dissolved emulsifying agents so as to act as a self-emulsifiable oil on addition to water.

The benzofuranyl esters may also be admixed with a wetting agent with or without an inert diluent to form a wettable powder which is soluble or dispersible in water, or may be mixed with the inert diluent to form a solid or powdery product.

Inert diluents with which the benzofuranyl esters may be incorporated include solid inert media comprising powdered or divided solid materials, for example, clays, sands, talc, mica, peat, fertilizers and the like, such products either comprising dust or larger particle size materials such as granules.

The wetting agents used may comprise anionic compounds such as for example soaps, fatty sulphate esters such as dodecyl sodium sulphate, octadecyl sodium sulphate and cetyl sodium sulphate, fatty aromatic sulphonates such as alkylbenzene sulphonates or butyl naphthalene sulphonate, more complex fatty sulphonates such as the amide condensation product of oleic acid and N-methyl taurine or the sodium sulphonate or dioctyl succinate.

The wetting agents may also comprise non-ionic wetting agents such as for example condensation products of fatty acids, fatty alcohols or fatty substituted phenols with ethylene oxide, or fatty esters and others of sugars or polyhydric alcohols, or the products obtained from the latter by condensation with ethylene oxide, or the products known as block copolymers of ethylene oxide and propylene oxide. The wetting agents may also comprise cationic agents such as for example cetyl trimethylammonium bromide and the like.

The physiologically active compositions according to the present invention may contain in addition to the benzofuranyl esters, other physiologically active materials such as herbicides, insecticides, fungicides and molluscicides. It has been found that particular advantages are obtained with mixtures with other herbicides.

Accordingly, a further embodiment of the present invention is for a herbicidal composition which comprises a mixture of the benzofuranyl esters as identified above and a second herbicide.

The second herbicide may be for example a phenoxyaliphatic acid, substituted urea, triazine, phenol, nitrile, bipyridylium compound, substituted benzoic acid, halogenated aliphatic acid, carbonate, thiocarbonate, chloroacetanide, diazine, arsenic compound or other herbicidal compound. In respect of selective herbicidal compositions for post-emergence use, the second herbicide is preferably a substituted phenoxyaliphatic acid; in respect of selective herbicidal compositions for pre-emergence use, the second herbicide is preferably a substituted urea or triazine.

The phenoxyaliphatic acid generally comprises alkyl and/or halogen substituted phenoxyaliphatic acids, and their salts, for example alkali metal, amine and alkanolamine salts, and functional derivatives, for example esters and amides. These compounds may be of activity such that they are recognised as commercial herbicides, or may be of only slight herbicidal activity. Examples of the substituted phenoxyaliphatic acids which may be mentioned include 2,4-dichlorophenoxyacetic acid, 2-methyl-4-chlorophenoxyacetic acid; 2,4,5-trichlorophenoxyacetic acid, gamma-2,4-dichlorophenoxybutyric acid, gamma-2-methyl-4-chlorophenoxybutyric acid, alpha-2-methyl-4-chlorophenoxypropionic acid.

The substituted urea generally comprises a tri- or tetra-substituted urea such as N'-parachlorophenyl-N,N dimethylurea, N-butyl-N'-(3,4-dichlorophenyl)-N-methylurea, N'-parachlorophenyl-O,N,N-trimethylisourea, N'-p-chlorophenyl-N-methoxy-N-methylurea, N,N-dimethyl-N'-phenylurea.

The triazine herbicide generally comprises a compound of the formula:

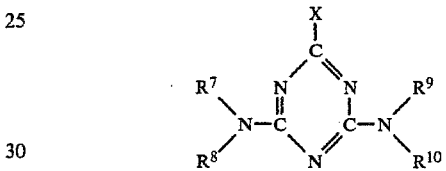

where X is a halogen, OY group or SY group, where Y is an alkyl group, and $R^7$, $R^8$, $R^9$ and $R^{10}$ are hydrogen or alkyl, such as 2-chloro-4,6-bisethylamino-1,3,5-triazine or 2-chloro-6-ethylamino-4-isopropylamino-1,3,5-triazine.

The phenol herbicide generally comprises 4,6-dinitro-o-cresol or pentachlorophenol. The nitrile herbicide generally comprises 3,5-diiodo-4-hydroxy-benzonitrile, 3,5-dibromo-4-hydroxybenzo-nitrile or 2,6-dichlorobenzonitrile. The bipyridylium herbicide generally comprises 1,1'-dimethyl-4,4'-bipyridylium dichloride or 1,1'-ethylene-2,2'-bipyridylium dibromide. The substituted benzoic acid herbicide generally comprises 2,3,6-trichloro-benzoic acid or 2-methoxy-3,6-dichlorobenzoic acid. The halogenated aliphatic acid herbicide generally comprises trichloroacetic acid or 2,2-dichloropropionic acid. The carbamate herbicide generally comprises isopropyl N-(3-chlorophenyl) carbamate or 4-chloro-2-butynyl N-(3-chlorophenyl) carbamate. The thiocarbamate herbicide generally comprises S-ethyl N,N-dipropylthio-carbamate, S-ethyl N,N-diisobutylthiocarbamate and S-(2,3-dichloroallyl) N,N-diisopropylthiocarbamate. the chloroacetamide herbicide generally comprise N,N-diallyl-2-chloroacetamide or N-isopropyl-2-chloroacetanilide. The diazine herbicide generally comprises 5-bromo-6-methyl-3-sec-butyluracil, 3-cyclohexyl-5,6-trimethyleneuracil or 1,2-dihydropyridazine-3,6-dione. The arsenic herbicide generally comprises a salt of methane arsonic acid or cacodylic acid. Other herbicides which may be used in such mixtures include aminotriazole,2,3-dichloro-1,4-naphthoquinone,4-amino-3,5,6-trichloropicolinic acid,2,6-dinitro-N,N-dipropyl-4-trifluoromethylaniline,6-chloro-2-trifluoromethylimidazo(4,5-b) pyridine and S,S,S-tributyl phosphorotrithioate.

A further embodiment of the invention comprises a process for the control of weeds, which comprises the use of a mixture of the benzofuranyl ester as identified and a second herbicide.

The ratio of the benzofuranyl ester to the second herbicide may vary over a wide range according to the particular compounds involved and the intended use. In general the ratio of benzofuranyl ester to second herbicide lies in the range 1:0.1 to 1:15.

These mixtures are of particular value in the control of weeds, and may be more effective and economical than the compounds used alone. In some cases synergism is observed.

In the use of the benzofuranyl esters as total herbicides, high rates of application, for example at least 10 pounds per acre, such as 10–25 pounds per acre, are required, unless the compounds are mixed with other active components, in which case the rate can be reduced.

In the use of the benzofuranyl esters as selective herbicides, the rate of application is much lower and may comprise for example 0.5–8 pounds per acre, such as 1–4 pounds per acre.

In the use of the benzofuranyl esters as plant growth regulants, low rates of application are required such as 0.1–4 pounds per acre, such as 0.5–1 pound per acre, according to the particular crop and use.

In the use of the esters as fungicides or insecticides for the treatment of plants, low rates of application will also be used such as 0.25–2 pounds per acre.

The rate of dilution of the active ingredient in the spray does not appear to be critical and may for example be based on volumes of 5–50 gallons per acre.

The esters may be used as plant growth regulants in standard ways. They can modify the natural growth characteristics of plants without killing them, and in particular are useful as growth retardants, e.g. of grass. Thus, they can be used on ornamental grass to retard growth so that less frequent mowing is required.

In the use of the esters as fungicides or insecticides for inanimate materials such as textiles the materials may be sprayed or dipped in a bath containing the esters. The treatment liquor suitably comprises an aqueous or organic solvent solution or suspension of the benzofuranyl ester containing for example 50–10,000 parts per million, and preferably 250–1,000 parts per million, of the benzofuranyl ester.

The benzofuranyl esters according to the present invention have been found of particular value in the control or growth retardation of annual and perennial grasses. Thus for example the benzofuranyl esters may be used for the control of couchgrass in crops such as brassica, potato, sugar beet and cereals such as: maize, or for the control of cyperus in cotton.

The following examples are given to illustrate the present invention; parts and percentages are by weight unless otherwise indicated.

EXAMPLE 1

To a stirred solution of 2,3-dihydro-3,3-dimethyl-5-hydroxy-2-piperidino-benzofuran (640 parts) in dry pyridine (1000 parts) at 5°–10° C. was added methanesulphonyl chloride (370 parts) over 1 hour. The mixture was stirred for a further 5 hours at about 10° C., then poured into water. The precipitated gum was washed with water (3×200 parts) by decantation, then triturated with ethanol (500 parts) when it set to a crystalline mass which was broken up, filtered, and the residue of crude ester was washed with aqueous ethanol (2:1) and sucked dry. Drying at 35° C. in vacuo over phosphoric oxide gave 2,3-dihydro-3,3-dimethyl-2-piperidinobenzofuran-5-yl methanesulphonate (660 parts, 78%) m.p. 97°–8° C.

Crystallisation of a sample from ethanol gave pure 2,3-dihydro-3,3-dimethyl-2-piperidinobenzofuran-5-yl methanesulphonate, m.p. 101°–3° C.

Found: C, 59.15; H, 7.35; N, 4.10: $C_{16}H_{23}NO_4S$ requires: C, 59.06; H, 7.13; N, 4.31%.

EXAMPLE 2

In a similar fashion were prepared the following compounds:

2,3-Dihydro-3,3-dimethyl-2-morpholinobenzofuran-5-yl methane-sulphonate, m.p. 111°–112° C. (in 80% yield).

2,3-dihydro-3,3-dimethyl-2-(4-methylpiperazino)benzofuran-5-yl methanesulphonate, m.p. 98°–9° C.

2,3-dihydro-3-ethyl-2-morpholinobenzofuran-5-yl methanesulphonate, m.p. 104°–7° C.

2,3-dihydro-3-ethyl-2-piperidinobenzofuran-5-yl methanesulphonate, m.p. 85°–8° C.

1,2,3,4,4a,9b-hexahydro-4a-morpholinodibenzofuran-8-yl methane-sulphonate, m.p. 101°–3° C.

2,3-dihydro-3,3-dimethyl-2-(dimethylamino)benzofuran-5-yl methanesulphonate, m.p. 64°–65° C.

2,3-dihydro-3,3-dimethyl-2-pyrrolidino-4,6-dichlorobenzofuran-5-yl methanesulphonate, m.p. 94°–95° C.

2,3dihydro-3,3,6,7-tetramethyl-2-pyrrolidinobenzofuran-5-yl methanesulphonate, m.p. 66°–67° C.

2,3-dihydro-3-hexyl-2-morpholinobenzofuran-5-yl methanesulphonate, m.p. 54°–57° C.

2,3-dihydro-3,3,6-trimethyl-2-morpholinobenzofuran-5-yl methanesulphonate, m.p. 134°–5° C.

2,3-dihydro-3,3-dimethyl-2-morpholino-6-methoxybenzofuran 5-yl methanesulphonate, m.p. 126°–8° C.

2,3-dihydro-3,3-dimethyl-2-morpholino-6-isopropylbenzofuran-5-yl methanesulphonate, m.p. 102°–3° C.

2,3-dihydro-3,3-dimethyl-2-morpholino-4-acetylbenzofuran-5-yl methanesulphonate, m.p. 156°–8° C.

2,3-dihydro-3,3-dimethyl-2-morpholino-6-chlorobenzofuran-5-yl methanesulphonate, m.p. 136°–8° C.

2,3-dihydro-3,3-dimethyl-2-morpholino-4,6-dichlorobenzofuran-5-yl methanesulphonate, m.p. 163°–5° C.

2,3-dihydro-3,3-dimethyl-2-morpholinobenzofuran-5-yl ethanesulphonate, m.p. 66°–70° C.

2,3-dihydro-3,3-dimethyl-2-morpholinobenzofuran-5-yl butanesulphonate, m.p. 62°–64° C.

2,3-dihydro-3,3-dimethyl-2-morpholinobenzofuran-5-yl 3-methoxypropanesulphonate, m.p. 73°–74° C.

2,3-dihydro-3,3-dimethyl-2-morpholinobenzofuran-5-yl chloromethanesulphonate, m.p. 130°–2° C.

2,3-dihydro-3,3-dimethyl-2-(4-methylpiperazino)benzofuran-5-yl ethanesulphonate, m.p. 82°–84° C.

2,3-dihydro-3,3-dimethyl-2-pyrrolidinobenzofuran-5-yl propanesulphonate, undistillable liquid.

2,3-dihydro-3,3-dimethyl-2-pyrrolidinobenzofuran-5-yl ethanesulphonate, undistillable oil.

2,3-dihydro-3,3-dimethyl-2-pyrrolidinobenzofuran-5-yl 2,2-dichloropropionate, undistillable oil.

2,3-dihydro-3,3-dimethyl-2-piperidinobenzofuran-5-yl 2,2-dichloropropionate, undistillable oil.

2,3-dihydro-3,3-dimethyl-2-morpholinobenzofuran-5-yl p-toluenesulphonate, m.p. 108° C.
2,3-dihydro-3,3-dimethyl-2-piperidinobenzofuran-5-yl p-toluenesulphonate, m.p. 98° C.
2,3-dihydro-3-ethyl-2-(4-methylpiperazino)benzofuran-5-yl methanesulphonate, m.p. 93°–94° C.
2,3,3a,8b-tetrahydro-3a-morpholino-1H-cyclopenta(b)benzofuran-7-yl methanesulphonate, m.p. 144°–6° C.
2,3-dihydro-3,3-dimethyl-2-morpholino-6,7-dichlorobenzofuran-5-yl methanesulphonate, m.p. 135°–136° C.
2,3-dihydro-3,3,6,7-tetramethyl-2-morpholinobenzofuran-5-yl methanesulphonate, m.p. 102°–103° C.

EXAMPLE 3

A cold suspension of 2,3-dihydro-3,3-dimethyl-5-hydroxy-2-pyrrolidino-benzofuran (18.5 parts) in dry ether (150 parts) and triethylamino (9.3 parts) was treated with methanesulphonyl chloride (10.5 parts) added all at once. After 0.75 hours the mixture was filtered and the filtrate was diluted to opalescence with petrol and filtered through kieselguhr. The filtrate was then evaporated to half volume and diluted with petrol giving white crystals (7.5 parts), m.p. 79°–81° C. of 2,3-dihydro-3,3-dimethyl-2-pyrrolidinobenzofuran-5-yl methanesulphonate.

Found: C, 57.55; H, 6.70; N, 4.30%: $C_{15}H_{21}NO_4S$ requires: C, 57.86; H, 6.80; N, 4.30%.

EXAMPLE 4

A suspension of 2,3-dihydro-3,3-dimethyl-2-morpholinobenzofuran-5-yl methanesulphonate (product of Example 2) (24.9 parts) in water (50 parts) and hydrochloric acid (22.4 parts) was rapidly heated to 90°–100° C. and then cooled after 2 minutes. The crude product was extracted into ether (3×60 parts) and the extracts washed with water (2×50 parts), dried with sodium sulphate and evaporated to leave a gum which crystallised to give 2,3-dihydro-3,3-dimethyl-2-hydroxybenzofuran-5-yl methanesulphonate, m.p. 69°–72° C. (16 parts)

EXAMPLE 5

The following were prepared by a similar method to that described in Example 4.
2,3-dihydro-3,3-dimethyl-2-hydroxy-6-methoxybenzofuran-5-yl methanesulphonate, m.p. 114°–6° C.
2,3-dihydro-3,3-dimethyl-2-hydroxy-6-isopropylbenzofuran-5-yl methanesulphonate, m.p. 103°–5° C.
2,3-dihydro-3,3,6,7-tetramethyl-2-hydroxybenzofuran-5-yl methanesulphonate, m.p. 109°–110° C.
2,3-dihydro-3,3-dimethyl-2-hydroxybenzofuran-5-yl ethane sulphonate, oily liquid.

EXAMPLE 6

A solution of crude 2,3-dihydro-3,3-dimethyl-2-hydroxybenzofuran-5-yl methanesulphonate (7.8 parts) in methanol (80 parts) containing sulphuric acid (2 drops) was boiled under reflux for one hour and then cooled. The solution was then neutralised with triethylamine and then evaporated to about quarter its volume. Water (10 parts) was then added to precipitate 2,3-dihydro-3,3-dimethyl-2-methoxybenzofuran-5-yl methanesulphonate, m.p. 69°–70° C.

Found: C, 53.15; H, 5.75: $C_{12}H_{16}O_5S$ requires: C, 52.94; H, 5.92%.

EXAMPLE 7

Using a similar method to that of Example 6, the following were prepared:
2,3-dihydro-3,3-dimethyl-2-ethoxybenzofuran-5-yl methanesulphonate, m.p. 70°–72° C.
2,3-dihydro-3,3-dimethyl-2-allyloxybenzofuran-5-yl methanesulphonate, m.p. 51°–52° C.
2,3-dihydro-3,3-dimethyl-2-(2-methoxyethoxy) benzofuran-5-yl methanesulphonate, m.p. 50°–53° C.
2,3-dihydro-3,3-dimethyl-2-ethylthiobenzofuran-5-yl methanesulphonate, liquid.
2,3-dihydro-3,3,6,7-tetramethyl-2-ethoxybenzofuran-5-yl methanesulphonate, m.p. 76°–8° C.
2,3-dihydro-3,3-dimethyl-2-isopropoxybenzofuran-5-yl methanesulphonate, m.p. 54°–56° C.
2,3-dihydro-3,3-dimethyl-2-propargyloxybenzofuran-5-yl methanesulphonate, liquid.
2,3-dihydro-3,3-dimethyl-2-(4-chloro-2-butynyloxy) benzofuran-5-yl methanesulphonate.
2,3-dihydro-3,3-dimethyl-2-(p-nitrophenoxy) benzofuran-5-yl methanesulphonate, m.p. 160°–3° C.
2,3-dihydro-3,3-dimethyl-2-ethoxybenzofuran-5-yl 3-methoxy-propanesulphonate, liquid.
2,3-dihydro-3,3-dimethyl-2-(2-chloroethoxy) benzofuran-5-yl methanesulphonate, liquid.
2,3-dihydro-3,3-dimethyl-2-ethoxybenzofuran-5-yl ethane-sulphonate, liquid.
2,3-dihydro-3,3-dimethyl-2-methoxybenzofuran-5-yl ethanesulphonate, liquid.
2,3-dihydro-3,3-dimethyl-2-isopropoxybenzofuran-5-yl ethanesulphonate, liquid.
2,3-dihydro-3,3-dimethyl-2-allyloxybenzofuran-5-yl ethanesulphonate, liquid.
2,3-dihydro-3,3-dimethyl-2-ethoxybenzofuran-5-yl butanesulphonate, m.p. 57°–9° C.

EXAMPLE 8

To a cooled solution of 2-hydroxy-2,3-dihydro-3,3-dimethylbenzofuran-5-yl methanesulphonate (8.0 parts) in dry pyridine (42 parts) was added benzoyl chloride (4.75 parts) at such a rate that the temperature did not exceed 10° C. After one hour the mixture was poured into a slight excess of dilute hydrochloric acid. The product was extracted with ether and the ethereal solution washed, dried with sodium sulphate and evaporated to give an oil which solidified on scratching. The solid was recrystallised from a mixture of benzene and light petroleum to give 2-benzoyloxy-2,3-dihydro-3,3-dimethylbenzofuran-5-yl methanesulphonate (5.1 parts), melting point 102°–104° C.

EXAMPLE 9

Using an analogous method to that described in Example 8 the following were prepared:
2-isobutyryloxy-2,3-dihydro-3,3-dimethylbenzofuran-5-yl methanesulphonate, m.p. 77°–79° C.
2-acetoxy-2,3-dihydro-3,3-dimethylbenzofuran-5-yl methanesulphonate, m.p. 84°–85° C.
2,3-dihydro-3,3-dimethyl-2-(phenoxyacetoxy)benzofuran-5-yl methanesulphonate, m.p. 103°–5° C.
2,3-dihydro-3,3-dimethyl-2-benzoyloxybenzofuran-5-yl ethanesulphonate, m.p. 101°–3° C.
2,3-dihydro-3,3-dimethyl-2-acetoxybenzofuran-5-yl ethanesulphonate, m.p. 56°–8° C.

EXAMPLE 10

A solution of 2-hydroxy-2,3-dihydro-3,3-dimethylbenzofuran-5-yl methanesulphonate (5 parts) in ether (85 parts) was treated with triethylamine (2.2 parts) and acetic anhydride (2.3 parts) at 10° C. and allowed to stand for 4 hours. The solution was then diluted with light petroleum (80 parts) and filtered. The filtrate was evaporated to give an oil which solidified. This was recrystallised from a mixture of chloroform and petroleum to give 2-acetoxy-2,3-dihydro-3,3-dimethylbenzofuran-5-yl methanesulphonate (2.5 parts), melting point 84°–85° C.

EXAMPLE 11

To a solution of 2-hydroxy-2,3-dihydro-3,3-dimethylbenzofuran-5-yl methanesulphonate (10 parts) in water (100 parts) containing sodium hydroxide (15 parts) was slowly added acetic anhydride (10 parts) with cooling to keep the temperature below 10° C. An oil separated which solidified on scratching. This was filtered off, washed with water, dried and recrystallised from 90% aqueous ethanol to give 2-acetoxy-2,3-dihydro-3,3-dimethylbenzofuran-5-yl methanesulphonate, melting point 84°–85° C.

EXAMPLE 12

2-ethoxy-2,3-dihydro-3,3-dimethylbenzofuran-5-yl methanesulphonate (7 parts) was treated with a mixture of acetic anhydride (20 parts) and sulphuric acid (0.6 parts) and left at 50° C. for two hours. The solution was then poured into an excess of ice and sodium bicarbonate. An oil precipitated which solidified and was filtered off and recrystallised from 90% aqueous ethanol to give 2-acetoxy-2,3-dihydro-3,3-dimethylbenzofuran-5-yl methanesulphonate (6.6 parts), melting point 83°–85° C.

EXAMPLE 13

A solution of 2-hydroxy-2,3-dihydro-3,3-dimethylbenzofuran-5-yl methanesulphonate (5 parts) in ether (85 parts) was treated at 10° C. with triethylamine (2.2 parts) and methanesulphonyl chloride (2.2 parts) and allowed to stand for 4 hours. The solution was then diluted with light petroleum (80 parts) and filtered through alumina. The filtrate was evaporated to dryness in vacuo and the residual oil solidified. Recrystallisation from a mixture of benzene and light petroleum gave 2,3-dihydro-3,3-dimethylbenzofuran-2,5-ylene bis-methanesulphonate, melting point 56°–58° C.

EXAMPLE 14

To a solution of 2-hydroxy-2,3-dihydro-3,3-dimethylbenzofuran-5-yl methanesulphonate (12 parts) in ether (46 parts) was added methyl isocyanate (4.5 parts) and triethylamine (0.3 parts). The solution was left at room temperature for two hours and the solvent evaporated off. The crude product was recrystallised from a mixture of benzene and light petroleum to give 2-methylcarbamoyloxy-2,3-dihydro-3,3-dimethylbenzofuran-5-yl methanesulphonate, melting point 126°–127° C.

Found: C, 48.55; H, 5.15; N, 4.65: $C_{13}H_{17}NO_6S$ requires: C, 49.52; H, 5.44; N, 4.44%.

EXAMPLE 15

The following was prepared by a similar method to that described in Example 14.

2,3-dihydro-3,3-dimethyl-2-(m-chlorophenylcarbamoyloxy)benzofuran-5-yl methanesulphonate, m.p. 142°–3° C.

EXAMPLE 16

A solution of 2-hydroxy-2,3-dihydro-3,3-dimethyl benzofuran-5-yl methane sulphonate in ether was reacted with triethylamine and methyl chloroformate. The product was worked up to separate 2,3-dihydro-3,3-dimethyl-5-methane sulphonyloxy benzofuran-2-yl methylcarbonate, melting point 88°–9° C.

In a similar way, using ethyl chloroformate in place of methyl chloroformate there was obtained 2,3-dihydro-3,3-dimethyl-5-methane sulphonyloxy benzofuran-2-yl ethyl carbonate, melting point 85°–7° C.

EXAMPLE 17

The following were prepared by a similar method to that described in Example 16.

2,3-dihydro-3,3-dimethyl-5-methanesulphonyloxybenzofuran-2-yl 4-chloro-2-butynyl carbonate, m.p. 70°–74° C.

2,3-dihydro-3,3-dimethyl-5-methanesulphonyloxybenzofuran-2-yl 2-methoxyethyl carbonate, m.p. 50°–52° C.

2,3-dihydro-3,3-dimethyl-5-methanesulphonyloxybenzofuran-2-yl isoamyl carbonate, m.p. 59°–61° C.

2,3-dihydro-3,3-dimethyl-5-ethanesulphonyloxybenzofuran-2-yl ethyl carbonate, m.p. 91°–3° C.

EXAMPLE 18

A solution of 2-hydroxy-2,3-dihydro-3,3-dimethylbenzofuran-5-yl methanesulphonate (20 parts), tertiary-butyl hydroperoxide (7 parts) and 1,4-dihydroxybenzene (0.5 parts) in benzene (800 parts) containing sulphuric acid (0.5 parts) was gently boiled under reflux for two hours. After cooling, triethylamine (1 part) was added and the filtered solution was concentrated below 20° C. in vacuo, to give 2-tert-butyl-peroxy-2,3-dihydro-3,3-dimethylbenzofuran-5-yl methanesulphonate (10 parts, 40% yield) as a yellow gum with infra-red and nuclear magnetic resonance spectra consistent with the assigned structure.

Analysis: Found: C,54.60; H, 5.95: $C_{15}H_{22}O_6S$ requires: C, 54.57; H, 6.67%.

EXAMPLE 19

A solution of 2-hydroxy-2,3-dihydro-3,3-dimethylbenzofuran-5-yl methanesulphonate (20 parts) in warm acetic acid (200 parts) was treated with 200 parts of a 20% aqueous solution of chromic oxide. After about 15 seconds the mixture was poured into water and the solution extracted with ether. The extracts were thoroughly washed with aqueous sodium bicarbonate, then dried and the solvent evaporated to give 2-oxo-2,3-dihydro-3,3-dimethyl-benzofuran-5-yl methanesulphonate (14 parts, 70% yield), melting point 120°–121° C. after recrystallisation from benzene-petroleum.

Analysis: Found: C, 51.80; H, 4.95: $C_{11}H_{12}O_2S$ requires: C, 51.56; H 4.72%.

EXAMPLE 20

The compounds listed in the table below were each formulated as an attaclay/sand dust and incorporated in John Innes I potting compost at a rate of 130 or 26 parts per million weight/volume active ingredient to soil (respectively approximately 50 or 10 lbs. active ingredient per acre cultivated to a depth of 2 inches). The treated soil samples were placed in anodised aluminium pans, 7½ ins. long×3¾ ins. wide×2 ins. deep. Seeds of peas (Pisum sativum), mustard (Sinapis alba), linseed (Linum usitatissmum), maize (Zea mays), oats (Avena sativa) and ryegrass (Lolium sp.) were sown in the treated soil, one species per pan, watered and placed in a controlled environment room (temperature 22° C., relative humidity 65-85%, artificial illumination 1200 foot-candles for 14 hours per day) for 21 days. The plants were then visually assessed for any growth regulatory or herbicidal effects, all differences from untreated controls being scored on a scale from 0 to 100 in which 0 signifies no effect and 100 signifies complete suppression. The activities against each species are tabulated below.

| Compound | Rate (lb/a) | Peas | Mustard | Linseed | Maize | Oats | Ryegrass |
|---|---|---|---|---|---|---|---|
| 2-tert-butylperoxy-2,3-dihydro-3,3-dimethylbenzofuran-5-yl methanesulphonate | 10 | 55 | 90 | 84 | 100 | 100 | 99 |
| 2-oxo-2,3-dihydro-3,3-dimethylbenzofuran-5-yl methanesulphonate | 50 | 97 | 98 | 94 | 100 | 100 | 98 |
| 2,3-dihydro-3,3-dimethyl-benzofuran-2,5-ylene bis-methanesulphonate | 10 | 98 | 97 | 97 | 98 | 99 | 98 |
| 2-acetoxy-2,3-dihydro-3,3-dimethylbenzofuran-5-yl methanesulphonate | 50 | 100 | 100 | 99 | 99 | 100 | 100 |
|  | 10 | 75 | 80 | 90 | 98 | 98 | 95 |
| 2,3-dihydro-3,3-dimethyl-5-methanesulphonyloxy-benzofuran-2-yl ethyl carbonate | 10 | 70 | 50 | 75 | 100 | 98 | 99 |
| 2-benzoyloxy-2,3-dihydro-3,3-dimethylbenzofuran-5-yl methanesulphonate | 50 | 99 | 95 | 99 | 98 | 100 | 100 |
| 2-isobutyryloxy-2,3-dihydro-3,3-dimethyl-benzofuran-5-yl methanesulphonate | 50 | 95 | 95 | 98 | 99 | 100 | 100 |
| 2,3-dihydro-3,3-dimethyl 2-piperidino-benzofuran-5-yl methanesulphonate | 50 | 85 | 99 | 99 | 99 | 100 | 100 |
| 2,3-dihydro-3,3-dimethyl 2-morpholino-benzofuran-5-yl methanesulphonate | 50 | 65 | 85 | 94 | 99 | 100 | 90 |
| 2,3-dihydro-3,3-dimethyl-2-ethoxybenzofuran-5-yl methanesulphonate | 50 | 100 | 100 | 100 | 100 | 100 | 100 |
| 2,3-dihydro-3,3-dimethyl-2-pyrrolidinobenzofuran-5-yl methanesulphonate | 10 | 70 | 70 | 100 | 98 | 100 | 91 |
| 2,3-dihydro-3,3-dimethyl-2-(4-methylpiperazino)benzofuran-5-yl methanesulphonate | 50 | 100 | 100 | 100 | 100 | 100 | 100 |
| 2,3-dihydro-3-ethyl-2-(4-methylpiperazino)-benzofuran-5-yl methane sulphonate | 50 | 25 | 85 | 65 | 100 | 100 | 98 |
| 2,3-dihydro-3,3-dimethyl-2-methoxybenzofuran-5-yl methanesulphonate | 50 | 100 | 100 | 100 | 100 | 100 | 100 |
| 2,3-dihydro-3,3-dimethyl-2-isopropoxybenzofuran 5-yl methanesulphonate | 50 | 80 | 100 | 98 | 99 | 100 | 85 |
| 2,3-dihydro-3,3-dimethyl-2-allyloxybenzofuran-5-yl methanesulphonate | 50 | 90 | 100 | 100 | 88 | 97 | 80 |
| 2,3-dihydro-3,3-dimethyl-2-(2-methoxyethoxy)benzofuran-5-yl methane sulphonate | 50 | 90 | 98 | 100 | 92 | 97 | 80 |
| 2,3-dihydro-3,3-dimethyl-2-propargyloxybenzofuran-5-yl methanesulphonate | 50 | 80 | 100 | 100 | 100 | 98 | 90 |
| 2,3-dihydro-3,3-dimethyl-2-morpholino-benzofuran-5-yl chloromethanesulphonate | 50 | 70 | 100 | 100 | 100 | 97 | 90 |
| 2,3-dihydro-3,3-dimethyl 2-hydroxybenzofuran-5-yl methanesulpho nate | 10 | 85 | 80 | 96 | 100 | 100 | 99 |
| 2,3-dihydro-3,3-dimethyl-2-morpholinobenzofuran-5-yl ethanesulphonate | 10 | 100 | 100 | 100 | 99 | 100 | 100 |
| 2,3-dihydro-3,3-dimethyl-2-ethoxybenzofuran-5-yl | | | | | | | |

-continued

| Compound | Rate (lb/a) | Peas | Mustard | Linseed | Maize | Oats | Ryegrass |
|---|---|---|---|---|---|---|---|
| ethanesulphonate | 50 | 90 | 100 | 98 | 100 | 100 | 97 |
| 2,3-dihydro-3,3-dimethyl-2-morpholino-6-chlorobenzofuran-5-yl methanesulphonate | 50 | 91 | 99 | 85 | 100 | 100 | 90 |
| 2,3-dihydro-3,3-dimethyl-2-(dimethylamino)benzofuran-5-yl methanesulphonate | 10 | 60 | 70 | 90 | 100 | 98 | 100 |

EXAMPLE 21

Seeds of peas, mustard, linseed, ryegrass, sugarbeet and oats were sown in anodised aluminum pans, 7½ inches long × 3¾ inches wide × 2 inches deep containing John Innes No. 1 potting compost. They were then watered and placed in a controlled environment room (22° C., 65-85% relative humidity and 14 hours/day artificial illumination at 1200 foot candles). Fourteen days after sowing, the seedlings were sprayed with 50% aqueous acetone solutions of the compounds listed in the table below at rates equivalent to 10 lbs. of active ingredient in 80 gallons per acre.

After seven days' growth in a controlled environment room the plants were visually assessed for herbicidal response by comparison with untreated controls. The table below gives the herbicidal activity on a 0–100 scale in which 0 represents no effect and 100 represents complete kill.

| Compound | Peas | Mustard | Linseed | Rye grass | Sugar beet | Oats |
|---|---|---|---|---|---|---|
| 2,3-dihydro-3,3-dimethyl-2-piperidino-5-benzofuranyl methanesulphonate | 45 | 65 | 65 | 70 | 24 | 75 |
| 2,3-dihydro-3,3-dimethyl-2-morpholino-5-benzofuranyl methanesulphonate | 45 | 65 | 65 | 72 | 30 | 75 |
| 2,3-dihydro-3,3-dimethyl-2-pyrrolidino-5-benzofuranyl methanesulphonate | 90 | 95 | 95 | 95 | 35 | 90 |
| 2,3-dihydro-3,3-dimethyl-2-(4-methylpiperazino)-5-benzofuranyl methanesulphonate | 45 | 48 | 65 | 60 | 20 | 75 |
| 2,3-dihydro-3-ethyl-2-piperidino-5-benzofuranyl methanesulphonate | 45 | 32 | 65 | 20 | 85 | |
| 2,3-dihydro-3-ethyl-2-morpholino-5-benzofuranyl methanesulphonate | 35 | 65 | 65 | 65 | 20 | 85 |

EXAMPLE 22

Aqueous acetone solutions containing 200 parts per million (ppm.) of the compounds listed in the table below together with 125 ppm. of a wetting agent were sprayed on to the leaves of young potato plants having seven fully expanded leaves, until the plants were completely wetted. After 24 hours, the treated plants were inoculated with sporangia of the disease potato blight (*Phytophthora infestans*). The plants were then placed in a water saturated atmosphere for 24 hours and then kept in a controlled environment room (Temperature 18° C., relative humidity 80–90%) for five days. At the end of this period, the percentage disease control was measured by comparison with control plants sprayed with a solution of wetting agent alone. Results were as follows:

| Compound | Control |
|---|---|
| 2,3-dihydro-3,3-dimethyl-2-pyrrolidinobenzofuran-5-yl methanesulphonate | 75% |
| 2,3-dihydro-3-ethyl-2-piperidinobenzofuran-5-yl methanesulphonate | 90% |
| 2,3-dihydro-3-ethyl-2-(4-methylpiperazino)benzofuran-5-yl methanesulphonate | 80% |

EXAMPLE 23

A wettable powder formulation was made up by grinding the following ingredients:

| | |
|---|---|
| 2,3-dihydro-3,3-dimethyl-2-ethoxybenzofuran-5-yl methanesulphonate | 20% |
| Diatomaceous earth | 70% |
| Hoe S2/268 (wetting/dispersing agent) | 5% |
| Dyapol PT (dispersing agent) | 5% |

(Hoe S2/268 contains a sodium salt of a sulphated fatty alcohol/ethylene oxide condensate. Dyapol PT is the sodium salt of a sulphonated cresol/urea/formaldehyde condensate).

EXAMPLE 24

A wettable powder formulation was made up by grinding the following ingredients:

| | |
|---|---|
| 2,3-dihydro-3,3-dimethyl-2-piperidinobenzofuran-5-yl methanesulphonate | 20% |
| China clay | 70% |
| Hoe S1/263 (wetting/dispersing agent) | 10% |

(Hoe S1/263 contains a mixture of a fatty alcohol/ethylene oxide condensation product and an ethylene oxide/propylene oxide block copolymer).

EXAMPLE 25

An aqueous suspension of 2-ethoxy-2,3-dihydro-3,3-dimethylbenzofuran-5-yl methane sulphonate was sprayed at a rate of 2 lbs per acre in 40 gallons on a plot in which cotton had been sown the previous day. After six weeks the cotton seedlings had developed with less than 15% of the weed infestation of unsprayed control plots in which the main weeds were Nutsedge (*Cyperus rotundus*) and Crabgrass (*Digitaria sanguinalis*).

EXAMPLE 26

1 ml. aliquots of acetone solutions of 2,3-dihydro-3,3-dimethyl-2-morpholino-benzofuran-5-yl methanesulphonate, 2,3-dihydro-3,3-dimethyl-2-(4-chloro-2-butynyloxy)benzofuran-5-yl methanesulphonate and 2,3-dihydro-3, 3-dimethyl-5-methane-sulphonyloxybenzofuran-2-yl 4-chloro-2-butynyl carbonate were applied to 9 cm. diameter filter papers placed in the bottom of 9 cm. diameter glass dishes at concentrations such as to produce deposits equivalent to 1000, 300 and 100 mg/sq. ft. The treated filter papers were then infested with adult house flies (*musca domestica*), covered with a glass lid and kept at 20° C. for 24 hours. At the end of this time all the flies were found to be dead.

EXAMPLE 27

An experiment was conducted on bent/fescue mixture grass in summer. The grass had not been treated with a fertilizer or chemical within the previous year. 2.8 Kg per ha of 2,3-dihydro-3,3-dimethyl-2-ethoxybenzofuran-5-yl methanesulphonate was sprayed on in water. Whereas untreated grass used as a control grew to a mean height of 6 cm in 4-5 weeks, the treated grass took over 11 weeks. The growth retardant effect is apparent.

It is to be noted that the benzofuranyl esters according to the invention where $R^4$ is hydroxy, in aqueous alkaline solution form the corresponding open chain compound by opening of the furan ring at the oxygen atom; these derivatives possess similar properties to the benzofuranyl esters and are also embraced in the present invention. The derivatives are in the form of a salt of the alkali; the alkali used is preferably an alkali metal hydroxide, and the salt is an alkali metal salt.

We claim:

1. A herbicidal or plant growth retardant composition comprising a herbicidal or plant growth retardant amount of a mixture of (A) a benzofuranyl compound of the formula

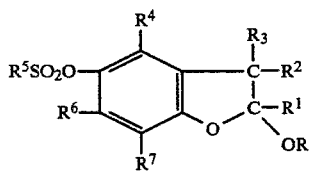

wherein R is a member selected from the group consisting of alkyl of 1 to 8 carbon atoms, alkenyl of 2 to 4 carbon atoms, monochloro alkenyl of 2 to 4 carbon atoms, alkynyl of 2 to 6 carbon atoms, monochloro alkynyl of 2 to 6 carbon atoms, alkoxyalkyl of 2 to 8 carbon atoms; $R^1$ is hydrogen or alkyl of 1 to 4 carbon atoms; $R^2$ and $R^3$ are the same or different and are hydrogen or alkyl of 1 to 4 carbon atoms; $R^5$ is alkyl of 1 to 4 carbon atoms or monochloro alkyl of 1 to 4 carbon atoms; and $R^4$, $R^6$ and $R^7$ are the same or different and are hydrogen, halogen or alkyl of 1 to 4 carbon atoms, and (B) a further herbicide, or plant growth retardant in admixture with at least one member of the group consisting of an inert carrier and a wetting agent.

2. A composition as claimed in claim 1 which contains a wetting agent.

3. A composition as claimed in claim 2 wherein the benzofuranyl compound is 2,3-dihydro-3,3-dimethyl-2-ethoxybenzofuran-5-yl methanesulphonate.

4. A herbicidal composition comprising a herbicidal amount of a mixture of (A) a benzofuranyl compound of the formula

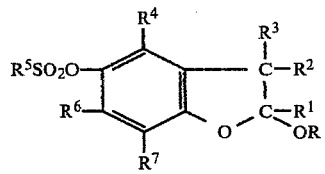

wherein R is a member selected from the group consisting of alkyl of 1 to 8 carbon atoms, alkenyl of 2 to 4 carbon atoms, monochloro alkenyl of 2 to 4 carbon atoms, alkynyl of 2 to 6 carbon atoms, monochloro alkynyl of 2 to 6 carbon atoms, alkoxyalkyl of 2 to 8 carbon atoms; $R^1$ is hydrogen or alkyl of 1 to 4 carbon atoms; $R^2$ and $R^3$ are the same or different and are hydrogen or alkyl of 1 to 4 carbon atoms; $R^5$ is alkyl of 1 to 4 carbon atoms or monochloro alkyl of 1 to 4 carbon atoms; and $R^4$, $R^6$ and $R^7$ are the same or different and are hydrogen, halogen or alkyl of 1 to 4 carbon atoms, and (B) a further herbicide, in admixture with at least one of the group consisting of an inert carrier and a wetting agent.

5. A composition as claimed in claim 4 which contains a wetting agent.

6. A composition as claimed in claim 4 wherein the weight ratio of benzofuranyl compound to other herbicide lies in the range 1:0.1 to 1:15.

7. A composition as claimed in claim 6 wherein the other herbicide is 3-cyclohexyl-5,6-trimethyleneuracil.

8. A composition as claimed in claim 6 wherein the other herbicide is a carbamate herbicide.

9. A composition as claimed in claim 6 wherein the other herbicide is a diazine herbicide.

10. A composition as claimed in claim 5 wherein R is alkyl of 1 to 8 carbon atoms.

11. A composition as claimed in claim 5 wherein $R^5$ is alkyl of 1 to 4 carbon atoms.

12. A composition as claimed in claim 5 wherein $R^2$ and $R^3$ are the same or different and are alkyl of 1 to 4 carbon atoms.

13. A composition as claimed in claim 5 wherein $R^4$, $R^6$ and $R^7$ are hydrogen.

14. A composition as claimed in claim 5 wherein R is alkyl of 1 to 8 carbon atoms, $R^5$ is alkyl of 1 to 4 carbon atoms, $R^2$ and $R^3$ are the same or different and are alkyl of 1 to 4 carbon atoms and $R^4$, $R^6$ and $R^7$ are hydrogen.

15. A composition as claimed in claim 5 wherein the benzofuranyl compound is 2,3-dihydro-3,3-dimethyl-2-methoxybenzofuran-5-yl methanesulphonate.

16. A composition as claimed in claim 5 wherein the benzofuranyl compound is 2,3-dihydro-3,3-dimethyl-2-isopropoxybenzofuran-5-yl methanesulphonate.

17. A compoistion as claimed in claim 5 wherein the benzofuranyl compound is 2,3-dihydro-3,3-dimethyl-2-allyloxybenzofuran-5-yl methanesulphonate.

18. A composition as claimed in claim 5 wherein the benzofuranyl compound is 2,3-dihydro-3,3-dimethyl-2-(2-methoxyethoxy)benzofuran-5-yl methanesulphonate.

19. A composition as claimed in claim 5 wherein the benzofuranyl compound is 2,3-dihydro-3,3-dimethyl-2-propargyloxybenzofuran-5-yl methanesulphonate.

20. A composition as claimed in claim 5 wherein the benzofuranyl compound is 2,3-dihydro-3,3-dimethyl-2-ethoxybenzofuran-5-yl ethanesulphonate.

21. A composition as claimed in claim 5 wherein the benzofuranyl compound is 2,3-dihydro-3,3-dimethyl-2-ethoxybenzofuran-5-yl methanesulphonate.

22. A method of combatting weeds at a locus infested or liable to be infested with them, or of retarding the growth of a plant at a locus were it is growing or is to grow, comprising applying to the locus an effective amount of a composition claimed in claim 1.

23. A method of improving crop yields which comprises applying a weed-combatting amount of a composition claimed in claim 1 pre-emergence or post-emergence to the crop or the area surrounding the crop.

24. A method of retarding plant growth which comprises applying to the plant or the soil surrounding the plant a plant growth retardant amount of a composition claimed in claim 1.

25. A method as claimed in claim 22 wherein the composition is as claimed in claim 2.

26. A method as claimed in claim 22 wherein the benzofuranyl compound is 2,3-dihydro-3,3-dimethyl-2-ethoxybenzofuran-5-yl methanesulphonate.

27. A method of combatting weeds at a locus infested or liable to be infested with them, comprising applying to the locus a weed-combatting amount of a composition claimed in claim 4.

28. A method as claimed in claim 27 wherein weeds are combatted in a crop.

29. A method as claimed in claim 28 wherein the crop is sugar beet.

30. A method as claimed in claim 29 wherein the benzofuranyl compound is 2,3-dihydro-3,3-dimethyl-2-ethoxybenzofuran-5-yl methanesulphonate.

31. A method as claimed in claim 27 wherein the composition is as claimed in claim 5.

32. A method as claimed in claim 27 wherein R is alkyl of 1 to 8 carbon atoms.

33. A method as claimed in claim 27 wherein $R^5$ is alkyl of 1 to 4 carbon atoms.

34. A method as claimed in claim 27 wherein $R^2$ and $R^3$ are the same or different and are alkyl of 1 to 4 carbon atoms.

35. A method as claimed in claim 27 wherein $R^4$, $R^5$ and $R^6$ are hydrogen.

36. A method as claimed in claim 27 wherein R is alkyl of 1 to 8 carbon atoms, $R^5$ is alkyl of 1 to 4 carbon atoms, $R^2$ and $R^3$ are the same or different and are alkyl of 1 to 4 carbon atoms and $R^4$, $R^6$ and $R^7$ are hydrogen.

37. A method as claimed in claim 27 wherein the benzofuranyl compound is 2,3-dihydro-3,3-dimethyl-2-methoxybenzofuran-5-yl methanesulphonate.

38. A method as claimed in claim 27 wherein the benzofuranyl compound is 2,3-dihydro-3,3-dimethyl-2-isopropoxybenzofuran-5-yl methanesulphonate.

39. A method as claimed in claim 27 wherein the benzofuranyl compound is 2,3-dimethyl-2-allyloxybenzofuran-5-yl methanesulphonate.

40. A method as claimed in claim 27 wherein the benzofuranyl compound is 2,3-dihydro-3,3-dimethyl-2-(2-methoxyethoxy)benzofuran-5-yl methanesulphonate.

41. A method as claimed in claim 27 wherein the benzofuranyl compound is 2,3-dihydro-3,3-dimethyl-2-propargyloxybenzofuran-5-yl methanesulphonate.

42. A method as claimed in claim 27 wherein the benzofuranyl compound is 2,3-dihydro-3,3-dimethyl-2-ethoxybenzofuran-5-yl ethanesulphonate.

43. A method as claimed in claim 27 wherein the benzofuranyl compound is 2,3-dihydro-3,3-dimethyl-2-ethoxybenzofuran-5-yl methanesulphonate.

44. A composition as claimed in claim 8 wherein the carbamate herbicide is isopropyl N-(3-chlorophenyl)-carbamate.

* * * * *